(12) United States Patent
Ho et al.

(10) Patent No.: US 10,590,374 B2
(45) Date of Patent: Mar. 17, 2020

(54) AUTOMATIC MULTI-TRAY AND MULTI-PLATE BIOREACTOR SYSTEMS FOR ADHERENT CULTURES

(71) Applicants: Timothy Ray Ho, Atlanta, GA (US); Lewis Ho, Lawrenceville, GA (US)

(72) Inventors: Timothy Ray Ho, Atlanta, GA (US); Lewis Ho, Lawrenceville, GA (US)

( * ) Notice: Subject to any disclaimer, the term of this patent is extended or adjusted under 35 U.S.C. 154(b) by 184 days.

(21) Appl. No.: 15/954,595

(22) Filed: Apr. 17, 2018

(65) Prior Publication Data
US 2018/0371394 A1 Dec. 27, 2018

Related U.S. Application Data

(60) Provisional application No. 62/523,797, filed on Jun. 23, 2017.

(51) Int. Cl.
*C12M 1/12* (2006.01)
*C12M 1/36* (2006.01)
*C12M 1/00* (2006.01)
*C12M 3/06* (2006.01)

(52) U.S. Cl.
CPC ............ *C12M 25/06* (2013.01); *C12M 23/04* (2013.01); *C12M 23/06* (2013.01); *C12M 23/50* (2013.01); *C12M 27/16* (2013.01); *C12M 29/06* (2013.01); *C12M 29/24* (2013.01); *C12M 29/26* (2013.01); *C12M 41/48* (2013.01)

(58) Field of Classification Search
CPC ....................................................... C12M 25/18
USPC ..................... 435/289.1–291.8, 294.1, 298.1
See application file for complete search history.

(56) References Cited

U.S. PATENT DOCUMENTS

| | | | |
|---|---|---|---|
| 7,604,987 B2 | 10/2009 | Hutmacher et al. | |
| 8,216,828 B2 | 7/2012 | Cattadoris et al. | |
| 8,602,636 B2 * | 12/2013 | Kauling | B01F 3/04269 366/105 |
| 10,344,257 B2 * | 7/2019 | Ho | C12M 27/20 |
| 2010/0210016 A1 | 8/2010 | Leuthaeuser et al. | |
| 2011/0263021 A1 * | 10/2011 | Stobbe | F04B 43/0736 435/398 |
| 2012/0086657 A1 | 4/2012 | Stanton et al. | |
| 2015/0017711 A1 | 1/2015 | Bennett et al. | |

* cited by examiner

*Primary Examiner* — Nina Bhat

(57) ABSTRACT

Described herein is an improved automatic bioreactor system utilizing a multi-tray or multi-plate cell culture vessel for cultivating adherent cells.

9 Claims, 12 Drawing Sheets

(1)

(2)

FIG 2
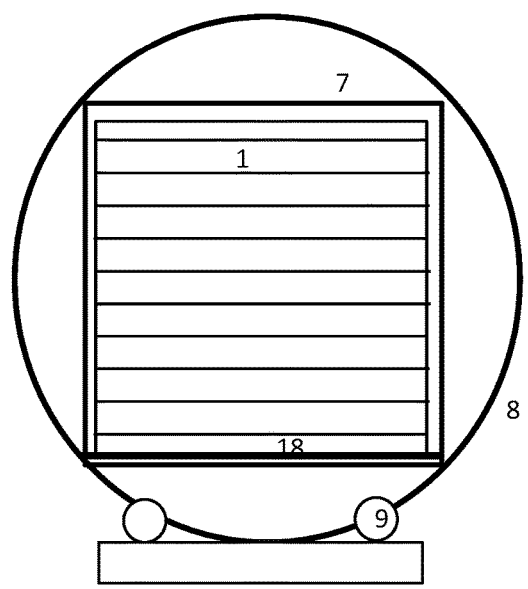
(1)
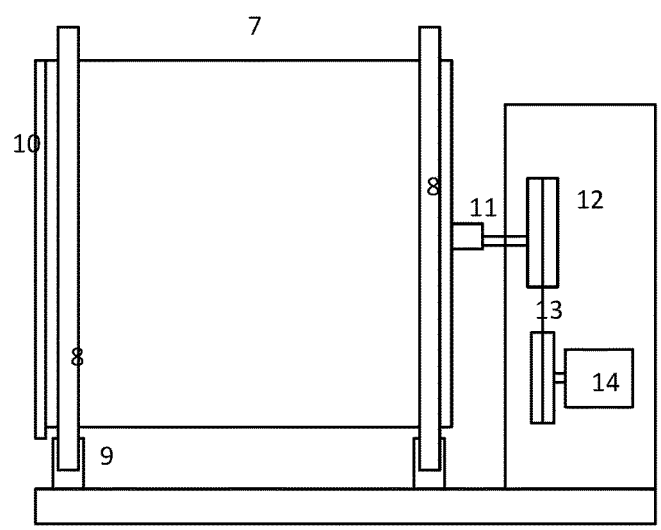
(2)

FIG 3A
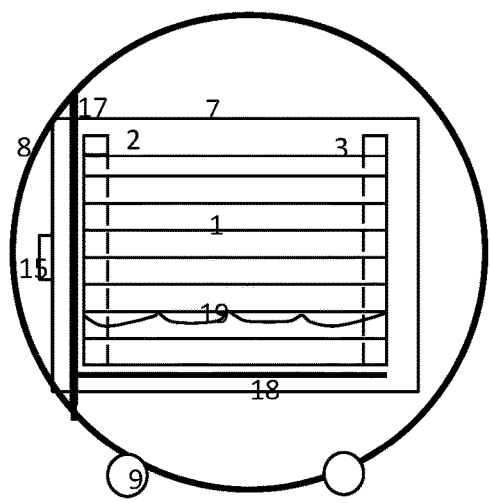
(a1)
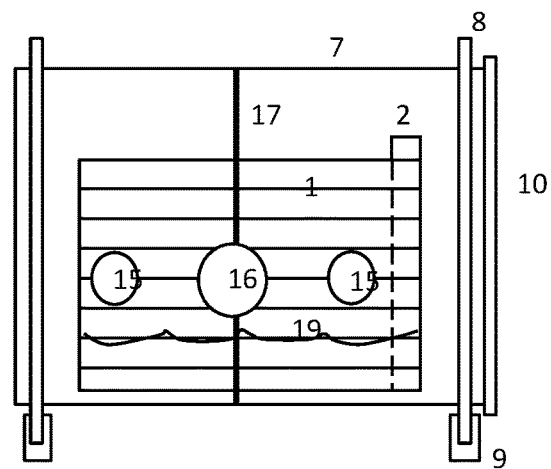
(a2)
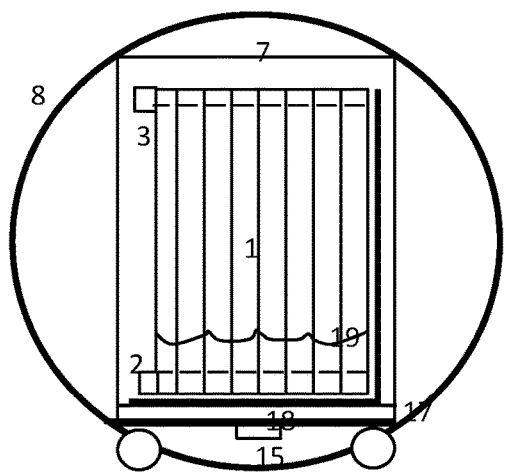
(b1)
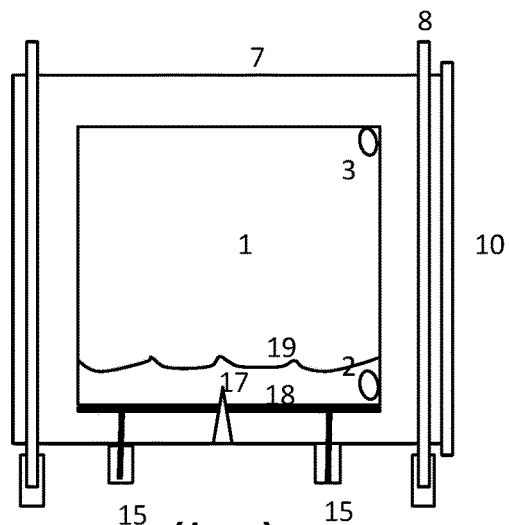
(b2)

(1)  (2)

FIG 4
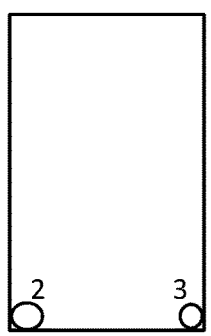 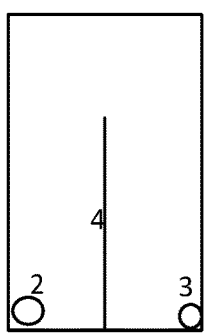 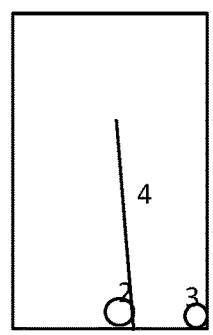 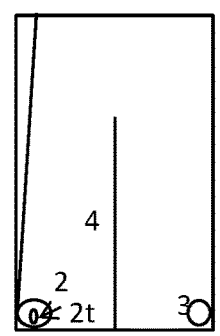 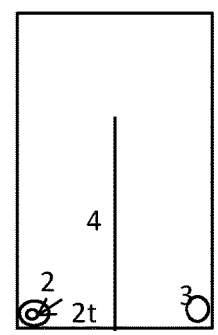
(1)　　(2)　　(3)　　(4)　　(5)

FIG 5A
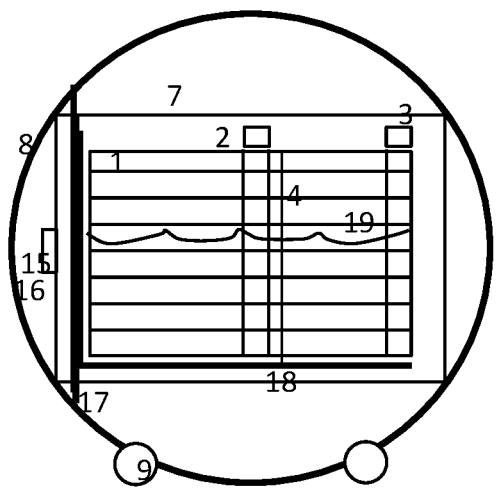
(a1)
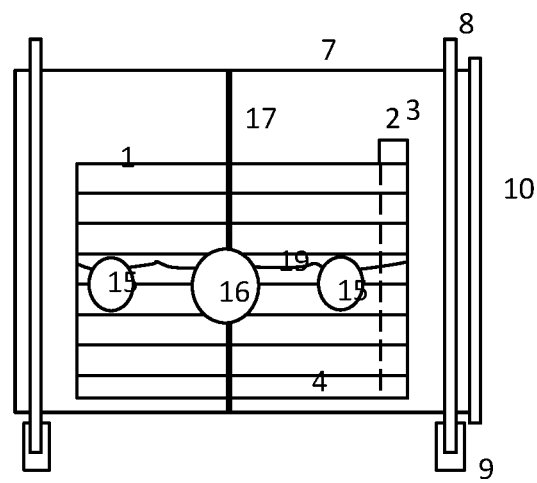
(a2)
(a) RA=0
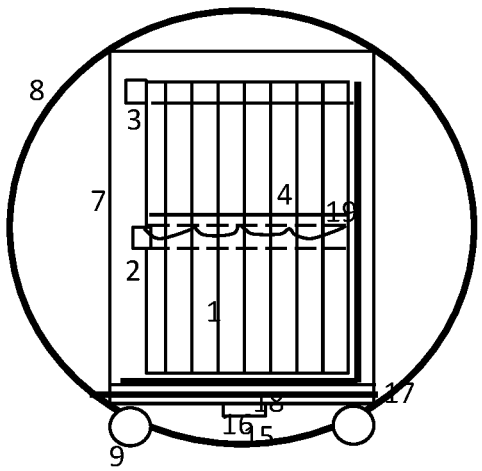
(b1)
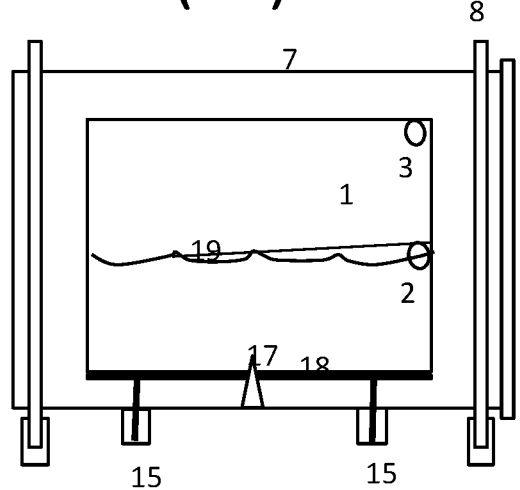
(b2)
(b) RA=90

(1) RA=90      (2) RA=-90

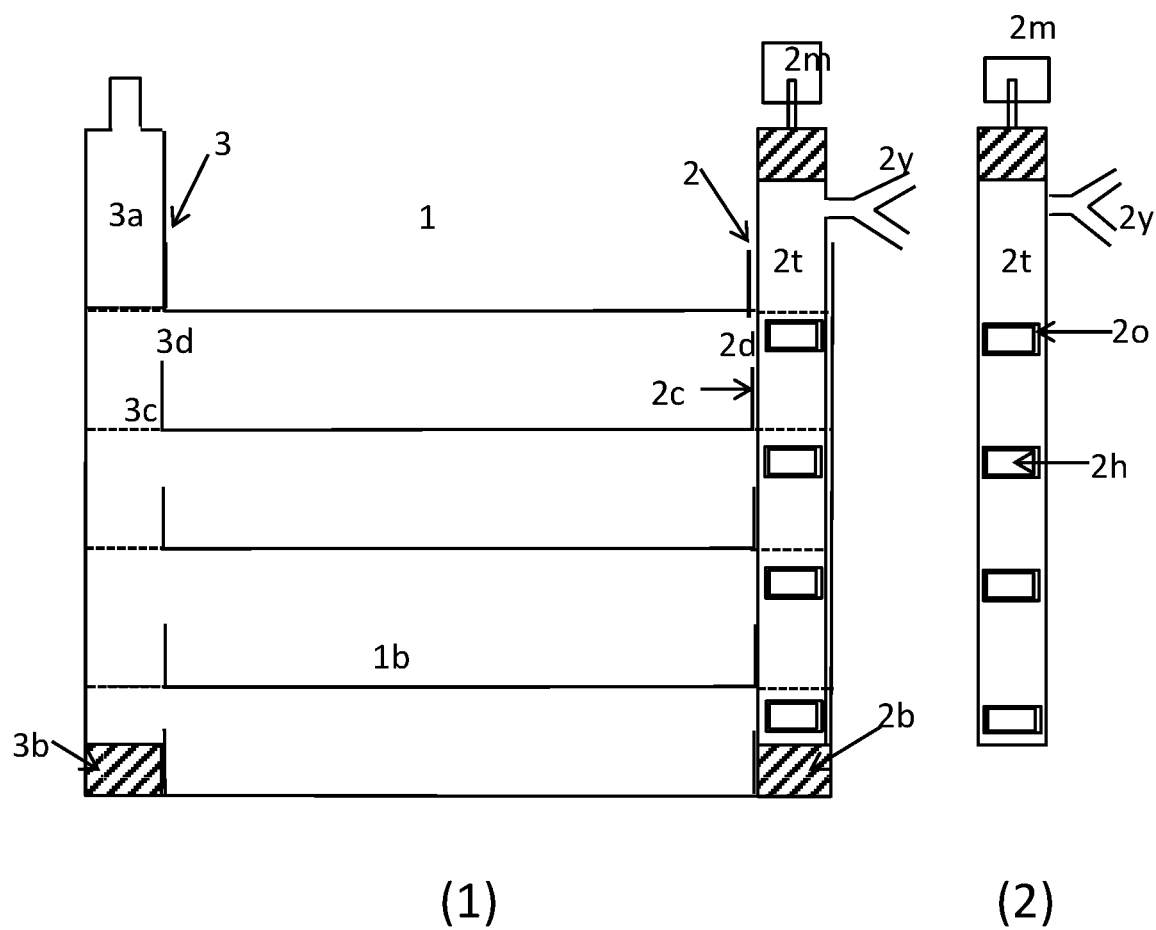

FIG 7A
RA=0
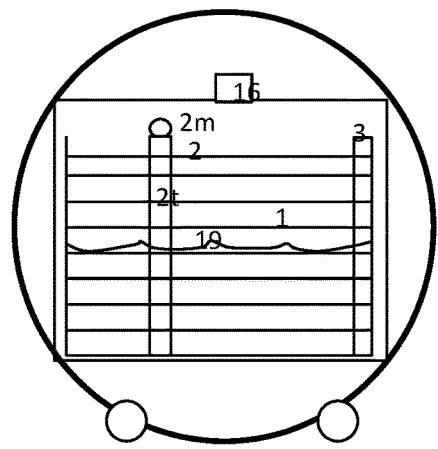
(1)
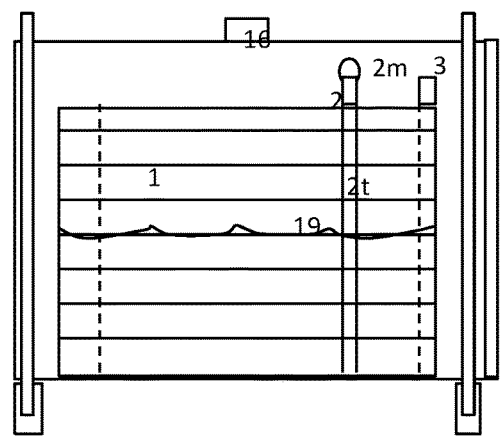
(2)
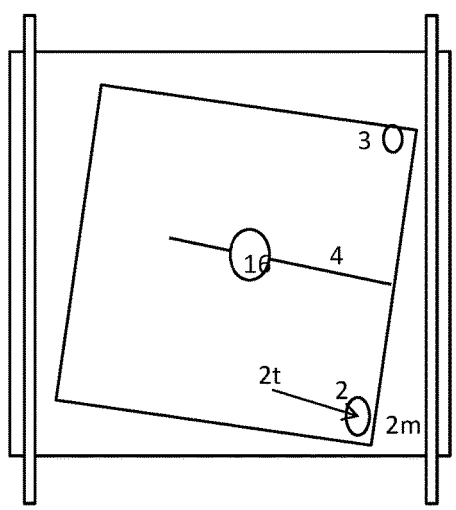
(3)

FIG 7B
RA=90
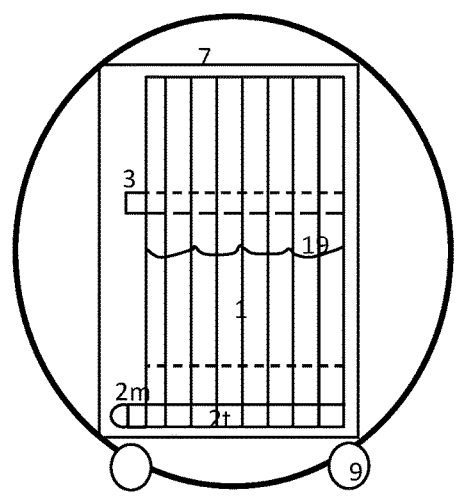
(1)
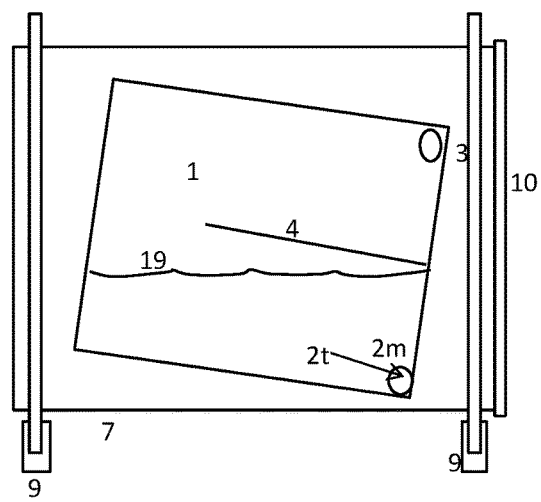
(2)
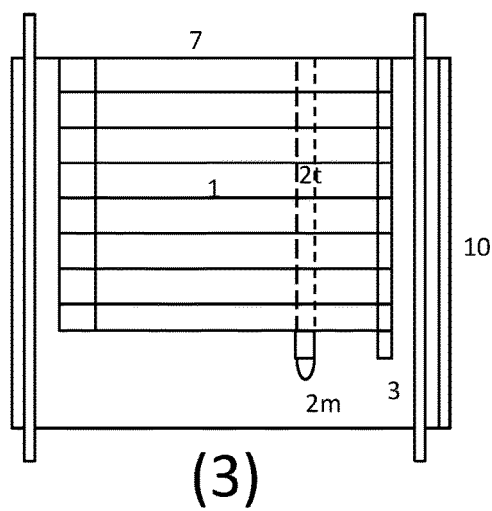
(3)

FIG 8A RA=0
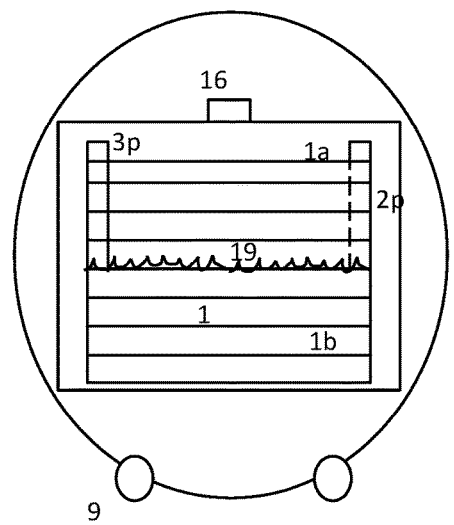
(1)
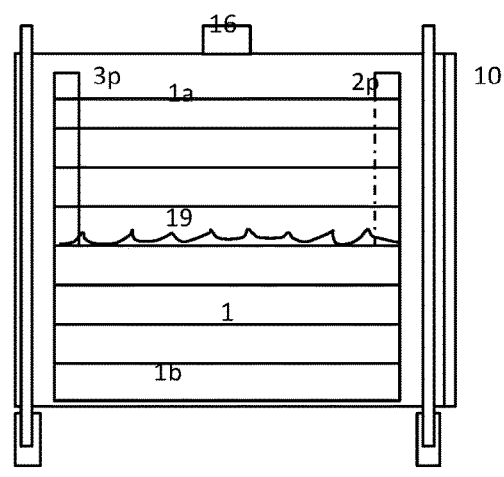
(2)
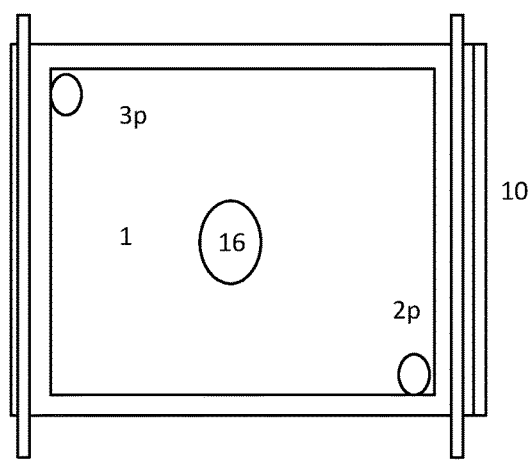
(3)

FIG 8B
RA=180
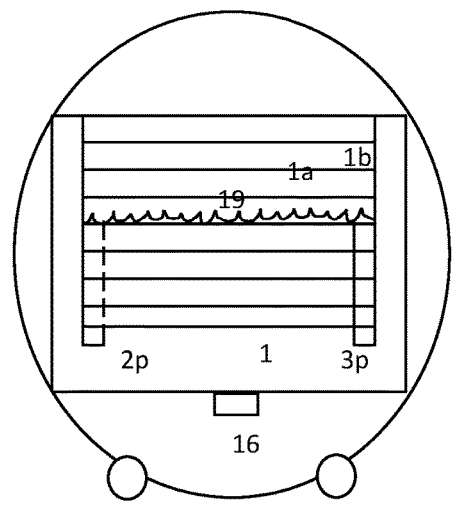
(1)
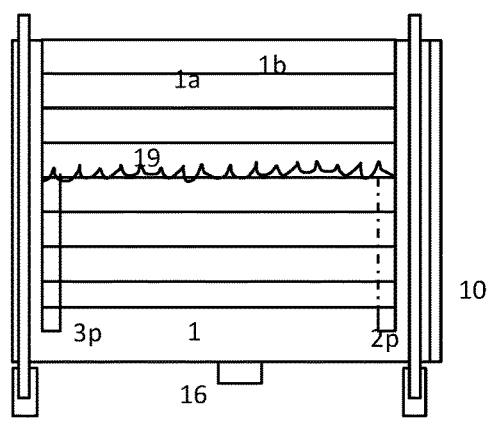
(2)
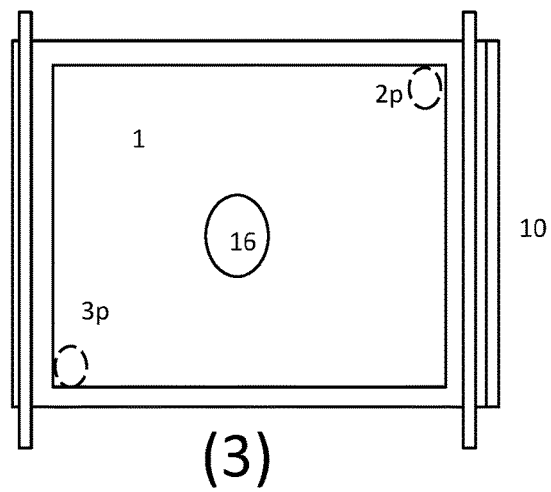
(3)

ial application No. 62/523,797 entitled Automatic Multi-tray
AUTOMATIC MULTI-TRAY AND MULTI-PLATE BIOREACTOR SYSTEMS FOR ADHERENT CULTURES This application claims the benefit of U.S. provisional application No. 62/523,797 entitled Automatic Multi-tray and Multi-plate Bioreactor Systems for Adherent Cultures, filed on Jun. 23, 2017

BACKGROUND

Adherent cells are always required to attach to some surface carrier for growth. T-Flasks and roller bottles are the most commonly used devices for these types of cell cultures in research use. Roller bottles have also been widely adopted for production use. However due to limited surface area available in each bottle, the use of roller bottle culture is labor intensive for production use. It is also lack of controllability and therefore gradually being replaced by other culture methods for adherent cell cultures such as methods using microcarrier and packed bed bioreactors which are commonly cultured in three dimensional (3D) carriers. However, many products, such as stem cells are preferentially required to be produced in two dimensional growth or as a monolayer. The simplicity of cell detachment and recovery of cells to meet the regulatory requirement is another reason to use the two dimensional growth culturing method. The debris of 3D fibrous carriers is not acceptable for cell therapy use. Therefore 2D culture method is still commonly used. The other reason is that most bioproducts derived from cell culture have been developed on 2D culture vessels such as the T-flask, and are ready to comply with regulatory requirements by remaining in the same 2D culture vessel for large scale production. To scale up from T-flask and roller bottle, the multi-tray bioreactors are the most commonly used systems available on the market today including Corning's Cellstack®, Hyperstack® and Thermo's Cell Factory® for static cultures.

For static cultures the multi-tray vessel with multiple parallel trays stacked as a vessel such as a 40 tray Cell Factory® can have a surface area of 25280 cm² in one vessel. However, the vessel can become very heavy, bulky, and labor intensive. Thermo therefore have developed automatic manipulators to perform the filling and emptying processes for the static culture. The manipulator employs a robotic arm to perform the manual operation by turning the vessel about two axes in three dimensions for filling and emptying. Then they need to use the cart to transport the filled vessel to an incubator for culturing. After culturing they need further to transport it to the manipulator and shaker for enzymatic treatment and detaching the cells. The entire operation is complicated, the footprint is large, the entire process is not integrated and still subject to the risk of contamination. Above all the system is extremely expensive (>$700 k) for manipulator, shaker, incubator and cart. This disclosure provides a unique solution enabling to perform the entire culturing process including filling, seeding, culturing, medium exchange, infection, transfection, sampling, cell detachment and harvesting automatically using the multi-tray culture vessels all in one closed system. US2010210016, US20060019388 and US20150017711A1 taught to rotate the culture chamber in two axes to perform each culturing process automatically. US 20090298164 and US20150017711A1 taught to use multi-layer vessel to perform static culture. US20120086657 and US20150017711A1 taught to apply system configuration to perform automation. None of the teachings however taught to use active gassing to the multi-tray 2D flat surface culture vessels for static culture and apply an integrated vessel to rotate only in one axis and use the same vessel as an incubator to perform the entire culturing process aforementioned all in one closed system.

For dynamic culture, Pall's Xpansion® is a multi-plate bioreactor using an agitated system to circulate the medium with constant flow over the surface plates and oxygenates by the diffusion of oxygen through silicon tubing. The efficiency of oxygenation is limited. Like Thermo's automated AMCF system, Xpansion® requires separate incubator for culturing and harvest station for cell detachment and recovery. Again it is not integrated and subject to the risk of contamination. Above all the system is very expensive. This disclosure alleviates all the limitation and complexity. It applies the most efficient and simple oxygenation method similar to roller bottle system and enables to make the system very simple. Above all, it is an integrated system and able to perform the entire culturing process all in one close system automatically.

SUMMARY

In one aspect, disclosed here is a bioreactor system comprising a culture vessel 1 comprising a closed vessel comprising at least one flat surface to culture the cells, at least one port to allow culture material or gas to flow into and out of the culture vessel 1a, a supporting vessel 7 comprising a tube positioned to lie along a longitudinal axis of the supporting vessel 7 wherein the tube has ends, at least one opening to allow culture material or gas to flow into or out of the supporting vessel 7, wherein a constant temperature is maintained inside of the supporting vessel 7; and a gassing assembly 32 comprising at least a gassing apparatus wherein the gassing apparatus 32 coupled to at least a gas ports of the at least one culture vessel and configured to apply actively the gas flowing into and out of the at least one culture vessel through a gas port of the culture vessel 1.

Also disclosed are systems of any preceding aspect, wherein the longitudinal tube of the supporting vessel 7 is most commonly in circular, oval or rectangular shapes but also in any other polygonal shapes.

Also disclosed are systems of any preceding aspect, wherein the bioreactor system further comprising a driving and rotating assembly 31 configured to rotate the supporting vessel 7 about the longitudinal axis and configured to hold and position the supporting vessel 7 and rotate only about the longitudinal axis along the plane perpendicular to the axis at any angle of less than 360 degrees, at rate of less than 50 rpm and at any holding time; a pumping apparatus 34 configured to pump culture material or gas into and out of the culture vessel 1 through at least one opening of the supporting vessel 7; a monitoring apparatus 35 configured to monitor one or more parameters of at least one of the culture vessel 1, the driving and rotating apparatus 31, the pumping apparatus 34, and the gassing apparatus 32 and a control apparatus 36 configured to coordinate at least one operation of at least one of the vessel assembly 1 & 7, the reservoir assembly 33, the rotating apparatus 31, the pumping apparatus 34, and the gassing apparatus 32 based on the one or more parameters. With all these combination this bioreactor system can perform the entire upstream process including filling, seeding, culturing, emptying, cell detaching, and harvesting all in one closed system.

Also disclosed are systems of any preceding aspect, wherein the supporting vessel 7 comprising further a platform 18 inside of the supporting vessel 7 secured on the wall of the supporting vessel 7 is configured to hold, secure and manipulate the at least one closed culture vessel 1; wherein the supporting vessel 7 is also used as an incubator for the at least one closed culture vessel 1 inside of the vessel.

Also disclosed are systems of the preceding aspect, wherein the platform 18 is a seesaw with the tilting angle of less than 180 degrees in each side of its pivot, wherein the pivot is secured on the supporting vessel 7.

Also disclosed are systems of any preceding aspect wherein the culture vessel 1 is a multi-tray culture vessel comprising at least two rectangular cell culture compartments having a lid, a bottom, two sides and two ends, arranged in a stacked orientation with respect to each other; and configured to allow cells to attach and grow as a monolayer on the bottom surface; at least one port for medium or gas in and out of the vessel, wherein each port is in gas/fluid communication among all compartments through a gas/fluid flow pathway which allows gas/fluid to flow through a manifold and into each culture compartment.

Also disclosed are systems of any preceding aspect wherein the culture vessel is the commercially available multi-tray culture vessels such as Thermal Fisher's Cell Factory® and Corning's Cellstack®.

Also disclosed are systems of any preceding aspect, wherein the platform 18 is stationary, fixed and secured on the supporting vessel 7.

Also disclosed are systems of the preceding aspect, wherein the culture vessel 1 is a multi-tray culture vessel comprising at least two rectangular cell culture compartments having a lid, a bottom, two sides and two ends, wherein the sides are longer than the ends, arranged in a stacked orientation with respect to each other; and configured to allow cells to attach and grow as a monolayer on the bottom surface and hold equal amount of medium and gas space above the cells in each compartment; at least one port for medium or gas in and out of the vessel, wherein each port is in gas/fluid communication among all compartments through a gas/fluid flow pathway which allows gas/fluid to flow through a manifold and into each culture compartment, and means enabling to open and block at least one gas/fluid communication among all compartments and the flow pathway which allows fluid to flow through a manifold and into each compartment;

Also disclosed are systems of the preceding aspect, wherein means enables to open or block the gas/fluid communication among all culture compartments and the flow pathway allowing fluid to flow through a manifold and into each tray is to use a motorized turncock 2t configured to fit into at least one manifold and enable to turn on and off the flow of culture fluid like a faucet.

Also disclosed are systems of the preceding aspect, wherein the culture vessel 1 is also a multi-plate culture vessel comprising a lid, a bottom, at least two sides and two ends each, wherein the culture vessel 1 has only one compartment and at least one flat surface plate, wherein the plate 1c is parallel to the lid and bottom of the culture vessel 1 and configured to secure individually or modularly to the vessel but not sealed and the each plate are freely communicated with other plates; wherein the culture vessel 1 comprises at least one port configured to allow the active gas and culture fluid to enter and exit the culture vessel 1.

BRIEF DESCRIPTION OF THE DRAWINGS

FIG. 2 shows a schematic diagram of (1) the front and (2) side views of the supporting vessel holding a multi-tray culture vessel inside and its driving/rotating assembly according to the present disclosure.

FIG. 3A shows the (a1) front and (a2) side views of the bioreactor system in the position of RA=0 and the (b1) front and (b2) side views in the position of RA=90; wherein a multi-tray culture vessel of Cell Factory or the like is placed on a platform of the supporting vessel according to the present disclosure.

FIG. 4 shows a schematic diagram of the top view of (1) a conventional multi-tray culture vessel and (2-5) four modified vessels with reduction of tray height or location of ports or addition of baffle according to the present disclosure.

FIG. 5A shows the (a1, b1) front and (a2, b2) side views of the bioreactor system in positions of RA=0 and RA=90 respectively; wherein a modified multi-tray culture vessel as described in FIG. 4(3) with reduction of tray height is placed on a platform of the supporting vessel according to the present disclosure.

FIG. 6 shows (1) the side view of a regular 4-tray culture vessel with addition of a turncock inserted in the manifold of inlet port and (2) the turncock according to the present disclosure.

FIG. 7A shows the (1) front, (2) side and (3) top views of the bioreactor system in the position of RA=0; wherein the modified multi-tray culture vessel as described in FIG. 4(5) with reduction of tray height and an addition of a motorized turncock in one manifold is placed on a platform of the supporting vessel according to the present disclosure.

FIG. 7B shows the (1) front, (2) side and (3) top views of the bioreactor system in the position of RA=90; wherein a modified multi-tray culture vessel as described in FIG. 4(5) is placed on a platform of the supporting vessel according to the present disclosure.

FIG. 8A shows the (1) front, (2) side and (3) top views of the bioreactor system in the position of RA=0; wherein the multi-plate culture vessel is placed on a platform of the supporting vessel according to the present disclosure.

FIG. 8B shows the (1) front, (2) side and (3) top views of the bioreactor system in the position of RA=180; wherein a multi-plate culture vessel is placed on a platform of the supporting vessel according to the present disclosure.

DESCRIPTION OF THE EMBODIMENT

Figure 1:
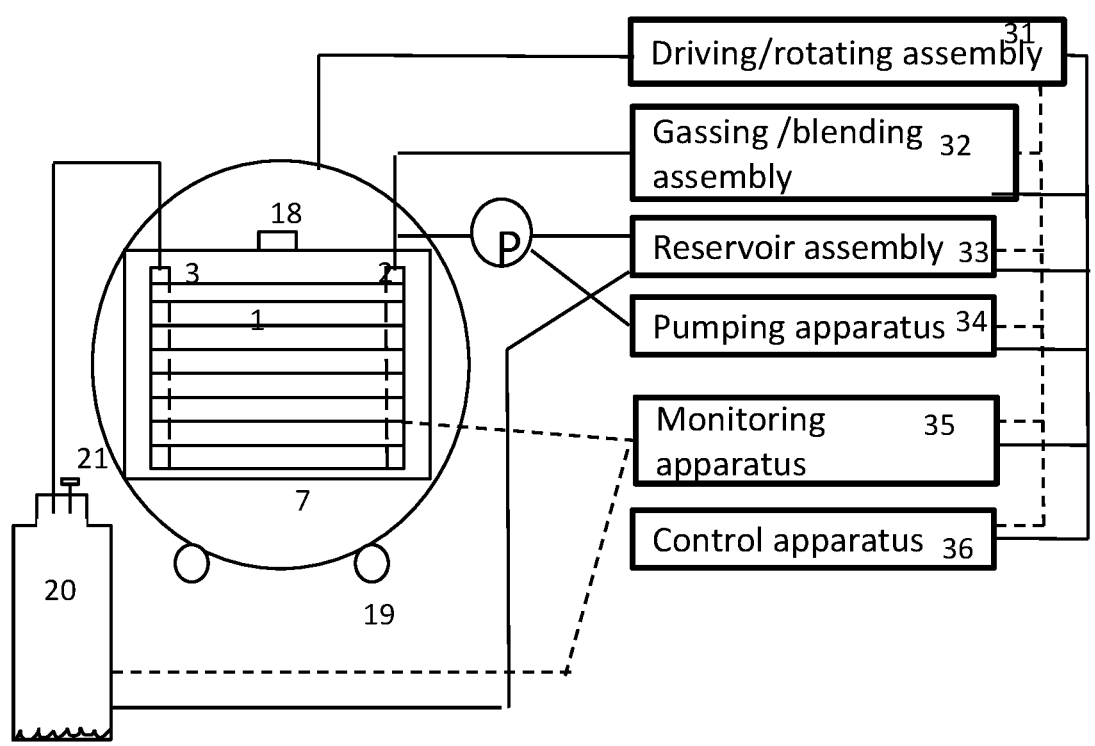
FIG. 1 shows a schematic diagram of the automatic bioreactor system using the multi-tray culture vessel according to the present disclosure.

In the following detailed description, reference is made to the accompanying drawings that form a part here of, and in which are shown by way of illustration several specific embodiments of apparatus, systems, and methods. It is to be understood that other embodiments are contemplated and may be made without departing from the scope or spirit of the present disclosure. The following detailed description, therefore, is not to be taken in a limiting sense. The embodiment as described here is a bioreactor system comprising:

1. A bioreactor system comprising:
   a) a vessel assembly comprising:
      a culture vessel comprising:
         a closed vessel comprising at least one flat surface to culture cells;
         at least one port to allow culture material or gas to flow into and out of the vessel;
      a supporting vessel comprising:
         a tube positioned to lie along a longitudinal axis of the tube, the tube having ends; at least one opening to allow culture material or gas to flow into or out of the tube and the ends;
         a platform secured inside of the tube and the ends is configured to hold, secure and manipulate the at least one closed culture vessel; and
         a constant temperature is maintained inside of the tube and the ends.
   b) a gassing assembly comprising:
      at least one gassing apparatus wherein the gassing apparatus is coupled to at least one gas port of the at least one culture vessel and configured to apply actively the gas flowing into and out of the at least one culture vessel through a gas port of the culture vessel.

As disclosed herein the bioreactor system wherein the culture vessel is a closed system wherein all openings of the culture vessel are connected with only tubing between the inside and outside of the vessel to perform the exchange of culture material including medium and cells through non-invasive valves or pumps during the entire operation so that there is no culture material ever inside of the culture vessel open directly to the external environment through human intervention.

As disclosed herein the bioreactor system wherein the culture vessel comprises at least one flat surface for cells to attach and grow and the ports for gas and culture material flowing into and out of the vessel.

As disclosed herein the bioreactor system wherein the supporting vessel is configured to position the culture vessel for performing the aforementioned processes including filling, culturing, medium exchange, emptying, detaching the cells and harvesting.

As disclosed herein the bioreactor system wherein the supporting vessel is temperature controlled and used as an incubator for the at least a closed culture vessel inside of the vessel. As disclosed herein the bioreactor system wherein the supporting vessel further comprises at least an electric fan with heating element to generate forced hot air to control the temperature inside of the vessel by the monitor apparatus and control apparatus described later.

As disclosed herein the bioreactor system wherein the supporting vessel is an open rigid vessel comprising at least a longitudinal tube and two ends made of single use or reusable material, wherein the shape of tube can be any shape including rectangular, circular, oval and polygonal, preferably, circular or rectangular; wherein the supporting vessel lies along its longitudinal axis and rotates about the axis along the plane perpendicular to the axis which is further illustrated in FIG. 2. The vessel is not closed wherein all openings of the culture vessel are not sealed but allow the tubing of the closed culture vessel to pass through its head plates and to connect to external sources including reservoir assembly, gassing apparatus, etc. As disclosed herein the bioreactor system wherein the gassing assembly is configured to supply actively the gas into the culture vessel and alter the gas composition by adjusting the flow rate of each supplied gas using a mass flow controller controlled by the control apparatus or manually regulated by a rotameter. Traditional culture method using a multi-tray vessel does not require active gassing but use passive gassing. The gas from the incubator diffuses through a filtered cap and a manifold into each tray of the culture vessel and the oxygen further diffuses through the medium and is transferred to the cells which are attached on the bottom surface of tray.

As disclosed herein wherein the supporting vessel comprising further a platform inside of the supporting vessel is configured to hold, secure and manipulate the at least a closed culture vessel by clamp, jaw, bolt, belt or the like in a fixed position. One type of the platforms is stationary and secured to the wall of tube and ends which will be further described herein with reference to FIGS. 7A, 7B, 8A and 8B. The other type is capable of moving like a see-saw of which the pivot is secured to the tube. This will be further described herein with reference to FIGS. 3A, 3B, 5A and 5B.

As disclosed herein the bioreactor system further comprises:
   a) a reservoir assembly configured to store the supply of gas, culture material, fresh medium, and reagents.
   b) a driving and rotating assembly configured to rotate the supporting vessel about the longitudinal axis and configured to hold and position the supporting vessel and rotate only about the longitudinal axis along the plane perpendicular to the axis at any angle of less than 360 degrees, at rate of less than 50 rpm and at any holding time;
   c) a pumping apparatus configured to pump culture material or gas into and out of the culture vessel through at least one opening of the supporting vessel;
   d) a monitoring apparatus configured to monitor one or more parameters of at least one of the culture vessel, the rotating apparatus, the pumping apparatus, and the gassing apparatus.
   e) a control apparatus configured to coordinate at least one operation of at least one of the vessel assembly, the reservoir assembly, the rotating apparatus, the pumping apparatus, and the gassing apparatus based on the one or more parameters.

As disclosed herein the bioreactor system comprises one reservoir assembly comprising at least one closed vessel made of single use or reusable material. The reservoir assembly comprises at least one vessel with proper mixing device such as shaker or agitator or air lifting or the likes. The reservoir assembly is for storage of fresh medium, spent medium, culture material from the culture vessel, inoculum, or the like or for retaining of exhaust gas; or for mixing, monitoring and controlling the physical properties of culture material. The vessel is made of single use material including polymeric material or the like as a bag, bottle, tank, etc. or of reusable material including glass, stainless steel etc. The reservoir assembly comprises at least one vent with air filter and one port.

As disclosed herein the bioreactor system comprises a pumping apparatus coupled to at least one medium port configured to allow fluidic culture material to flow in and out of at least one cell culture vessel; the pumping apparatus contains at least one pump to transport the fluid in and out the vessel. Ideally the pump is a peristaltic pump or the like which has no parts that contact the fluid to maintain system integrity. The fluidic culture material can be inoculum, fresh medium, spent medium, seeded medium, virus solution, enzymatic and washing reagents, etc.

As disclosed herein the bioreactor system comprises a driving and rotating assembly configured to hold and position the supporting vessel and the platform inside of the vessel; the driving/rotating assembly is driven by a DC stepping motor that moves in discrete steps. The motor has multiple coils which are organized in groups named "phases". By energizing each phase in sequence, the motor rotates one step at a time. With computer controlled stepping, a very precise positioning and/or speed control is achieved. Other options available for positioning control depend on the type of actuator driving the system include stepping motor, pneumatic, brake motor, clutch brake, DC servo system and AC servo system, preferably the stepping motor. The supporting vessel is coupled to the shaft of the motor directly or through a driven chain including belt, chain, gear and the like. The driving/rotating assembly is configured to rotate the at least one supporting vessel or culture vessel about the longitudinal axis along the plane perpendicular to the axis at any angle of less than 360 degrees, to stop at any angle or position, to hold at any position for any length of time and rotate at any rate of less than 50 rpm, preferably less than 10 rpm. The driving/rotating assembly also comprises a driving/rotating mechanism to drive the seesaw platform where the culture vessel is placed on, wherein the driving/rotating mechanism is a linear actuator which is configured to tilt the platform to right and left about the axis perpendicular to longitudinal and along the plane perpendicular to the ground by any angle of less than 180 degrees, preferably less than 15 degrees. For static culture the driving/rotating assembly rotates the supporting vessel between 0 to 90 degrees and allows manipulating of the culture vessel to fill and empty automatically for seeding, culturing, medium exchange, sampling, cell detachment and harvesting all in one closed system.

As disclosed herein the bioreactor system comprises a monitoring apparatus configured to monitor one or more parameters of the culture vessel including culture material of the at least a culture vessel, the supporting vessel, reservoir assembly, pumping apparatus, gassing assembly and driving/rotating assembly. The parameters of culture vessel, supporting vessel, reservoir assembly and culture material of the at least a cell culture vessel include all physical, chemical, biophysical, biochemical, biological properties such as temperature, pH, pressure, dissolved oxygen (DO), dissolved carbon dioxide (DCO2), glucose, lactate, glutamine, glutamate, ammonium, pH, sodium, potassium, osmolality, protein, nucleic acid, cell count, cell viability, cell morphology and the like for interest of process monitoring, development and optimization. The parameters are monitored by sensors, biosensors, on-line or off-line biochemical or biophysical analyzers, imaging devices and the like. In the reservoir assembly is monitored its pressure for system integrity and filter blockage using pressure sensor. In the pumping apparatus using peristaltic pump or the like is monitored its pumping rate by the roller speed of the pump. In the gassing/blending assembly is monitored the flow rates of each gas by each mass flow meter. In the driving/rotating assembly is monitored its rotating angle, position and rate of the supporting vessel and the platform by movement of stepping motor or linear actuator.

As disclosed herein the bioreactor system comprises a controlling apparatus connected wired or wirelessly to the culture vessel, supporting vessel, reservoir assembly pumping apparatus, gassing/blending assembly, driving/rotating assembly and monitoring apparatus wherein the control apparatus is configured to coordinate the positioning and movement of the supporting vessel and at least a culture vessel using the driving/rotating assembly, the pumping of culture material into and out of the at least a culture vessel using the pumping apparatus, the passing of respiratory gas in and out of at least a culture vessel and pressurization of the culture vessel using the gassing/blending assembly. The control apparatus comprises at least a central digital computer used as programmable logic controller (PLC) or the like to control the position, rocking rate, angle and holding time of the rocking apparatus; the pumping rate of the pumping apparatus; the gas composition and gas flow rate of the gassing assembly; the control of operating parameters including temperature, pH, DO, pressure or the like and also the chemical, biophysical, biochemical, or biological parameters monitored by the monitoring apparatus. The bioreactor system described herein provides a fully automated solution to accomplish all processes including filling, seeding, culturing, medium exchange, emptying, sampling, cell detachment, sampling and harvesting all in a closed system.

In FIG. 1 is illustrated the schematic diagram of the bioreactor system wherein the culture vessel 1 is secured in the supporting vessel 7 and rotated by the driving/rotating assembly 31, monitored and controlled by monitoring 35 and control apparatus 36, wherein the culture vessel 1 is connected through two ports 2 and 3 with flexible tubing or the likes to the supply of respiratory gas, culture material, fresh medium, reagents or the storage of spent fluid, medium, gas and reagents from the reservoir assembly 33 and to exit to a vessel 20 with air filter 21 in the reservoir assembly 33, wherein the culture material includes cells, medium or the likes, wherein the supply of gas, culture material, fresh medium, reagents and removal of spent gas, medium, culture material, reagents are transported through the flexible tubing by a peristaltic pump or the likes from the pumping apparatus 34, wherein the entire culture system is closed without human intervention and the entire culturing process including filling, culturing, emptying, infection, transfection, sampling, cell detachment and harvesting is totally automatic in a closed system. As a bioreactor this innovated system possess all the features of its functionality and controllability to perform all control and process strategies for better productivity and product quality including feedback control, fed-batch, semi-continuous process or the likes.

As disclosed herein the open rigid supporting vessel is configured to be supported by set of rollers while the vessel is driven and rotated in circular motion. For a circular vessel the roller rolls against the wall of vessel. For a rectangular vessel two solid rings are welded to the vessel in both ends and served as the tracks for the roller to rotate on as shown in the schematic diagram FIG. 2 with (1) the front view of the vessel and (2) side view of the driving/rotating assembly 31 wherein the rectangular supporting vessel 7 is welded with two solid rings 8 in the front and rear of the supporting vessel 7, wherein the rings 8 are used to sit on a set of four rollers 9 for supporting and as tracks for the supporting vessel 7 to roll on. In the front of the supporting vessel 7 is a clear cover 10 or a cover with window to view inside of the supporting vessel 7, wherein a closed culture vessel 1 is secured inside on a platform 18. In the rear of the supporting vessel 7 is welded with a coupling shaft 11 and a pulley 12 which is connected to another pulley by a belt 13 or chain driven by a stepping motor 14 which is controlled by the control apparatus to perform the positioning and rotating motion. Alternatively the rollers 9 can be driven by the stepping motor and indirectly rotating the supporting vessel 7 by the rollers.

Figure 3B:
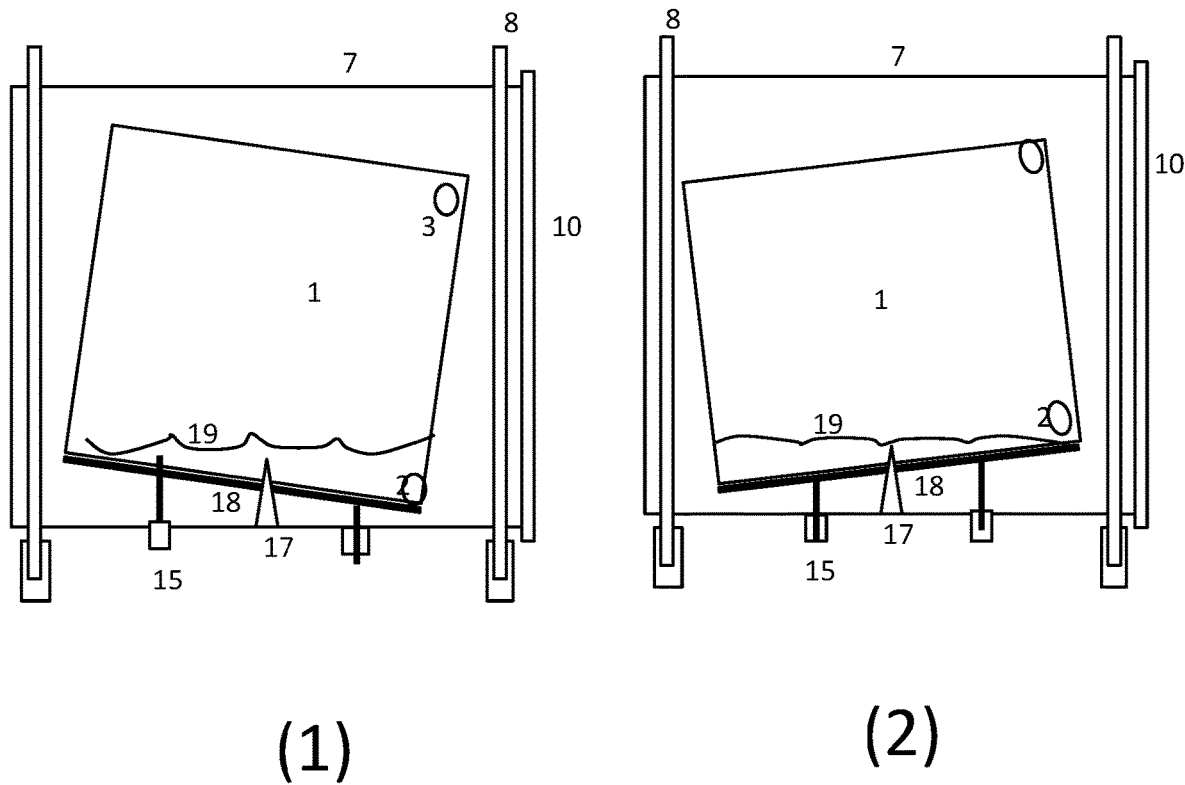
FIG. 3B shows the side view of the bioreactor system in the position of RA=90; wherein the platform on which a multi-tray culture vessel of Cell Factory or the like is placed on is tilted to (1) the right and (2) the left by the linear actuators according to the present disclosure.

As disclosed herein the platform 18 is a moving seesaw platform with the tilting angle of less than 180 degrees in each side of its pivot 17, wherein the pivot 17 is secured on the wall of the supporting vessel 7, wherein both ends of the platform 18 are connected and driven by two linear actuators 15 to lift the platform 18 up and down in an angle of less than 180 degrees, preferably less than 15 degrees about the axis perpendicular to longitudinal axis and along the plane perpendicular to the ground as the supporting vessel 7 at the position designated as the rotating angle of RA=90 or RA=−90 (RA=0 is the position where the platform 18 is horizontal and parallel to the ground) as described in FIG. 3B. The linear actuator creates motion in a straight line from a rotating motor and is commonly used to lift an object. The platform 18 allows the culture vessel 1 to turn about the second axis in a simple manner which is further described in FIGS. 3B and 5B.

As disclosed herein is the bioreactor system wherein the culture vessel is a multi-tray culture vessel comprising at least two rectangular cell culture compartments having a lid, a bottom, two sides and two ends, arranged in a stacked orientation with respect to each other; and configured to allow cells to attach and grow as a monolayer on the bottom surface; at least a port for medium or gas in and out of the vessel, wherein each port is in gas/fluid communication among all compartments through a gas/fluid flow pathway which allows gas/fluid to flow through a manifold and into each culture compartment.

As disclosed herein the culture vessel is typically the commercially available multi-tray culture vessel such as Cell Factory®, Cellstack® or the likes. The largest vessel of Cell Factory® and Cellstack® is comprised of 40 identical rectangular trays of about 205 mm×330 mm×16 mm each with two molded manifolds associated with two ports in each corner of an end stacked and sealing bonded together to form a 40 tray vessel, wherein each tray forms a separate compartment from others but remains connected with others by the manifold, wherein the bottom of opening of each manifold molded in each tray is about 3 mm above the bottom of each tray so that each tray can hold the recommended fluid height of about 3 mm when the tray sits flat horizontally for culturing, wherein the opening allows the gas/fluid freely flowing in and out of the compartment through the manifold. In the standard manual operation one of the ports is for filling and emptying the fluid and another port is for passive gas exchange. The vessel requires turning about two axes in three dimensions in order to fill the medium evenly in each tray and also to empty the culture material. This is due to the communication among all trays through the common manifold. This will be further described herein with reference to FIG. 3A and FIG. 3B.

In the following FIG. 3A is illustrated the operating sequence of a regular multi-tray culture vessel represented by Cell Factory® as shown in FIG. 4(1) in performing the basic automated static culturing process from filling to culturing and emptying. The remaining processes including virus infection, DNA transfection, cell detachment, sampling and harvesting use the same basic automatic operation but in different sequences. FIG. 3A shows (a1) the front, (a2) the side view of a regular multi-tray vessel situated in this disclosed system at position of RA=0, wherein the position of the vessel is represented by the rotating angle (RA) of the vessel. The position of RA=0 is the initial position, wherein the culture vessel 1 is placed inside of the supporting vessel 7, wherein the vessel is in upright normal position and the bottom is parallel to the ground, two ports on the lid of the vessel are in the front of the supporting vessel 7. As the vessel 7 is rotated counterclockwise in 90 degrees, the position is designated as RA=90. The port 2 is connected through a Y and tubing to a gassing apparatus 32 and a medium reservoir assembly 33 while port 3 is connected with a vessel 20 and an air filter 21 as shown in FIG. 1. The platform 18 is perpendicular to longitudinal axis and the bottom of the culture vessel 1 wherein the pivot 17 of the seesaw platform 18 is secured on the supporting vessel 7. The platform 18 is connected to both of linear actuators 15 and tilted up or down by the linear actuators 15 which are mounted outside of the supporting vessel 7 and activated and controlled by the control apparatus for the angle, position, speed and holding time. A heating fan 16 is mounted underneath the platform 7 and controlled by the controller in the control assembly. At this position a given amount of medium and inoculum sufficiently enough to fill each tray with medium height of 2-3 mm is fed in by a pump apparatus 34 such as peristaltic pump controlled by the control apparatus 36. Then proceed to turn the supporting vessel 7 and vessel 1 to the position of RA=90. FIG. 3A further shows the (b1) front and (b2) side views of the regular multi-tray vessel situated in this disclosed system at position of RA=90; The supporting vessel 7 is turned 90 degrees to the position of RA=90 wherein the port 2 is in the lowest position. At this position the control apparatus 36 activates the linear actuators 15 to tilt the platform 18 to the right lowering the gas inlet port 2 to the lowest position of this vessel as shown in FIG. 3B(1), wherein the culture fluid is equilibrated among all trays. Then the platform 18 is tilted to the left allowing the fluid to flow away from the port 2 as shown in FIG. 3B(2) and remain equilibrated in all trays. Then the supporting vessel 7 is activated to turn back to RA=0 position wherein each tray remains to have equal amount of fluid in the tray, then further activate the actuator 15 to return the platform 18 back to the original position parallel to the side of the supporting vessel 7 for culturing.

To further illustrate the automation of other culturing processes, the cell detachment process is described as an example in the following: A cell detachment process occurs when the culturing process is finished and recovery of cells is required. Commonly an EDTA solution wash and Trypsin enzymatic treatment are required. After culturing the culture fluid is emptied from port 2 at position of RA=90 as the platform 18 is tilted to the right. Then the washing solution is pumped in by a peristaltic pump of the pumping apparatus through port 2 for a given amount sufficiently enough to fill each tray by 2-3 mm height of solution, then tilt the platform 18 to the left and let the fluid away from port 2 and then turn the supporting vessel 7 back to RA=0 position while all trays having equal amount of washing solution and then tilt platform 18 back to original position. At his point each tray will fill with washing solution about 2-3 mm height in each tray as did in the previous filling process of culture fluid. Then the control apparatus 36 activates the driving/rotating assembly 31 to rock the supporting vessel 7 at higher speed of <10 rpm and at a given angle of about 20 degrees back and forth for five minutes, then turns the vessel to position of RA=90, tilts the platform 18 to the right wherein the port 2 is in the lowest position and drain the entire washing EDTA solution. Then followed with a given concentration of trypsin solution and amount just enough to cover the bottom surface of each tray using the same procedure described above for washing solution. Then allows the enzymatic solution to soak the monolayer of cells on each tray and incubate for given amount of time and then drains the solution as before and finally followed with the medium or buffer solution with the same filling procedure and rocking the supporting vessel 7 and vessel 1 with a higher rocking rate of <10 rpm for a given amount of time to shake off the cells from the tray and complete the cell detachment and recovery process.

As disclosed herein the multi-tray culture vessel is a modification of typical commercially available multi-tray culture vessel by alteration of height, dimension, and location of gas exit port of each tray, adding baffle or divider or curved edges in the gas flow pathway in each compartment. Because this disclosure applies active gassing rather than passive gassing as conventional vessel, it requires only a shallow gas space to apply the constant laminar flow of gas over the culture medium surface for gas exchange. For active gassing the bioreactor applies gas to flow into the vessel with positive pressure and requires shallow gas space to get the gas passing through. Laminar flow is a flow regime characterized by high momentum diffusion and low momentum convection. It is a gentle flow without disturbing the liquid surface on each tray of the vessel. For passive gassing the vessel allows gas flowing into the gas space of vessel by diffusion and thus requires larger gas space to spread throughout the vessel. Therefore the gas space of each tray of culture vessel can be significantly reduced from regular 12-15 mm to 2 mm by this disclosed system while maintaining the suggested medium height of 2-3 mm. This implies that the height of each tray can be reduced from 16 mm to 5-6 mm or by about 3 folds. Another benefit of the active gassing is to allow the length of the vessel to extend beyond the length of regular vessel along the longitudinal axis to any practical length without concerning the difficulty of gas diffusion as seen in the regular passive gassing vessel so that the production capacity of each vessel can be substantially increased. However, this would require the modification of culture vessel as described herein with reference to FIG. 4. In FIG. 4 is shown the top views of (1) the regular and (2-5) its four modified multi-tray vessels.

FIG. 4(1) is the top view of a regular vessel 1 represented by Cell Factory® wherein the vessel comprises multiple identical trays with two sides, two ends and a bottom each stacked and bonded together, wherein two ports 2 and 3 with a manifold each are located in the two corners of end of the vessel, wherein all trays are connected through the manifolds having openings to each tray.

FIG. 4(2) is the modified vessel with a divider 4 in the center of the vessel and extended from the short end where two ports 2 and 3 are located toward the opposite of other end but having enough space allowing the gas flow turning around the edge of divider 4 and returning back to the starting end but in the exit port 3, wherein the divider 4 is molded beneath the bottom of each tray, wherein the height of divider 4 is high enough to submerge in the liquid so that the gas flow is confined in the gas space above the liquid.

Figure 5B:
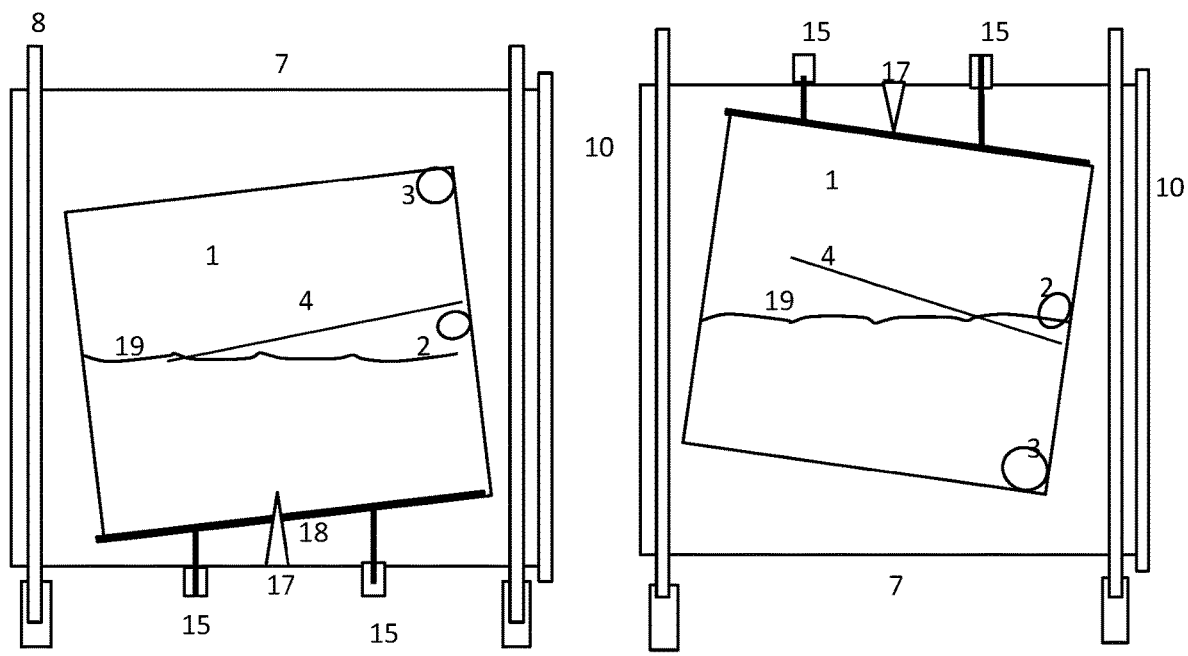
FIG. 5B shows the side view of the bioreactor system in positions of (1) RA=90 and (2) RA=−90; wherein the platform on which the modified multi-tray culture vessel as described in FIG. 4(3) is placed on is tilted by the linear actuators to left for (1) equilibrating and to right for (2) draining according to the present disclosure.

FIG. 4(3) is another modified vessel with relocation of the gas exit port 3 to the opposite diagonal corner of inlet port 2 so that the gas flow can travel the longest distance across the compartment in each tray. As disclosed herein the height of each tray can be reduced by about ⅓ of the regular vessel or the height of gas space can be reduced to equal or less than that of liquid space because of the active gassing. As a result the percentage of liquid volume to the total volume in each tray can be substantially increased and thus the tilting angle of platform is required to increase greatly to avoid the communication manifold among the trays away from the liquid during the rotating in order to achieve even distribution of the liquid in each tray. To minimize the tilting angle of the platform in order to be facilitated by the simple mechanism using the linear actuators in this system, the medium inlet port 2 is relocated to about the center position in the end where the port 2 is above the liquid level as shown in FIGS. 5A and 5B when the vessel is at position of RA=90 and a gas outlet port 3 is added in the other corner of the same side as the inlet port located, and also at least a divider 4 is added between two gas ports to even the gas flow path from an end to the other end.

FIGS. 4(4) and (5) are further modified with vessel based on FIG. 4(2) comprising a turncock 2t in the medium inlet port 2 which are described herein with reference to FIGS. 6 and 7A and 7B. In FIG. 5 are illustrated the operating sequence of the modified multi-tray culture vessel as described by FIG. 4(3) in performing the basic automated static culturing process from filling to culturing similar to that for a regular vessel shown in FIG. 3. FIG. 5A shows a(1), b(1) the front and a(2), b(2) the side views of the modified vessel situated in this disclosed system at position of RA=0, RA=90 respectively. At position of RA=90 as shown in FIG. 5B(1) the platform 18 is tilted to left for equilibrating the liquid volume in each tray wherein all ports are above the liquid. But it requires to rotate 90 degrees clockwise to position of RA=−90 as shown in FIG. 5B(2), and tilt the platform 18 to the right for emptying wherein port 2 is in the lowest location in the liquid.

As disclosed herein is the bioreactor system, wherein the platform is stationary, fixed and secured on the wall of the vessel. The platform holds and secures the culture vessel and requires no rotation in the second axis as the previous case when the culture vessel is further modified so that there is no need to turn on and off the gas/fluid communication among all culture compartments of the vessel. The further modification of the modified multi-tray culture vessels with addition of an opening/blocking mechanism in the manifold of the medium inlet port is shown in FIG. 4(4) and FIG. 4(5). In FIG. 4(4) is the modified vessel with addition of a slanted inner side 4, relocation of the exit port 3 and reduction of the tray height. FIG. 4(5) is the same as FIG. 4(2) but with reduction of the tray height and addition of a turncock in the inlet port. This modified vessel will be described further herein with reference to FIGS. 7A and 7B. The another modification of the culture vessel is a multi-plate culture vessel comprising a lid, a bottom, at least two sides and two ends each, wherein the culture vessel has only a compartment and at least a flat surface plate, wherein the plate is parallel to the lid and bottom of the culture vessel and configured to secure individually or modularly to the vessel but not sealed and the each plate are freely communicated with other plates not only through the manifold as the previous multi-tray vessel; wherein the vessel comprises at least a port configured to allow the active gas and culture fluid to enter and exit the culture vessel. The modified multi-plate culture vessel will be further described herein with reference to FIG. 8A and FIG. 8B.

As disclosed herein the modified multi-tray cell culture vessel has means enabling to open and block the gas/fluid communication among culture compartments and the flow pathway which allows fluid to flow through a manifold and into all compartments. Without the means it requires turning the vessel in the second axis to disconnect the communication of the fluid in the manifold of the medium inlet port before turning back to the culturing position in order to maintain an even volume of culture material in each compartment. With the means to open and block the flow pathway in the manifold, the vessel requires only rotate about an axis to evenly maintain the culture fluid in each tray and needs not to tilt the platform for block the manifold. In previous disclosure the means is to use a pneumatic means which is not as effective as the present disclosure. In this disclosure the mechanical means is to use a turncock or the likes configured to fit into the manifold and enabling to turn on and off the flow of fluid like a water faucet as shown in FIG. 6. Other mechanical means includes creating an air lock by a flexible body in the manifold or the likes. In FIG. 6 is shown (1) the side view of the modified multi-tray culture vessel 1 with two ports 2 and 3 and two manifold 2c and 3c, wherein the multi-tray vessel comprises 5 identical trays stacked and bonded together to form a 4-tray vessel, wherein the molded manifold 2c, 3c of each tray has an opening 2d, 3d of which the bottom is about 3 mm above the bottom 1b of each tray, wherein a connector 3a is inserted and bonded to the top of manifolds 3 and two stoppers 2b, 3b are inserted and bonded to the bottom of manifolds of the culture vessel 1, the inlet port 2 is inserted with a turncock 2t; wherein the turncock 2t is driven by a motor 2m mounted on the top of the turncock 2m, wherein the inlet of the turncock 2m is connected with a Y connector 2y for gas and culture fluid respectively; (2) the turncock 2t comprising an open tube like a stem of a faucet with holes 2h corresponding to each opening of the manifold in each tray and an O ring 2o around each hole.

In FIGS. 7A and 7B are illustrated the operating sequence of a modified multi-tray culture vessel as described in FIG. 4(5) with height reduction of each tray and addition of the motorized turncock in the medium inlet manifold to perform the basic static culturing process from filling to culturing and emptying without requiring to rotate the vessel in the second axis.

FIG. 7A shows the (1) front, (2) side and (3) top view of the multi-tray bioreactor system comprising a modified multi-tray vessel containing equal volume of liquid and gas in each tray at position of RA=0 as described previously in FIG. 3A except the liquid level 19 is in half of the vessel because of the reduction of tray height and the addition of a motorized turncock 2t mounted on the manifold 2c in port 2 so that the turncock 2m can be turned on or off by a motor 2m to open or stop the communication among trays for fluid and gas flow. The modified multi-tray vessel 1 is placed and secured on a fixed platform 18 inside of the supporting vessel 7 but with a small angle off the side as shown in FIG. 7A(3). The port 2 is connected through a Y connector 2y and tubing to a gas apparatus 32 and a medium reservoir assembly 33. The platform 18 is fixed and welded to the supporting vessel 7. A heater fan 16 is mounted on the top of the supporting vessel 7 to control the temperature of inside of the supporting vessel 7 by a controller of the control apparatus. At this position a given amount of medium and inoculum sufficient to fill each tray with medium height of 2-3 mm is fed in by a peristaltic pump from the pump apparatus controlled by a control apparatus. Then proceed to turn the supporting vessel 7 and vessel 1 to the position of RA=90. FIG. 7B shows the (1) front, (2) side and (3) top view of the modified multi-tray vessel at position of RA=90. At this position because the preset angle of the culture vessel 1 on the fixed platform 18 the gas inlet port 2 is already in the lowest location of this vessel 1 as shown in FIG. 7B(2), wherein the culture fluid is equilibrated. The motorized turncock 2t is then activated to close the manifold to disconnect the fluid communication and the supporting vessel 7 is then activated to turn back to RA=0 position wherein each compartment has equal amount of fluid in the tray, both vessel 7 and vessel 1 are then returned back to the position RA=0 and ready for static culturing at this position. With modification of the modified vessel described in FIG. 4(4) with addition of a turncock 2t in port 2, the vessel can be placed on the platform 18 in alignment with the longitudinal axis without requirement of a slanted angle as described above with reference to FIGS. 7A and 7B. It is because the slanted angle is already built inside of the modified vessel 1. Likewise the length of vessel 1 can also be extended to increase the surface area per vessel.

As disclosed herein the modified multi-tray cell culture vessel with blocking mechanism is configured to be used for both static and dynamic cultures. In the static culture both the cells attached on the culture surface of the vessel and the medium remain static under a controlled environmental condition such as a $CO_2$ incubator or the like for the entire culture time. In the other hand, for the dynamic culture the cells attached on the culture surface of the vessel constantly or frequently moving against the medium or vice versa under a controlled environmental condition such as a $CO_2$ incubator or the like for the entire culture process. Conventional culture method using T-flask is an example of static culture and roller bottle culture method is example of dynamic culture. In this disclosure the modified multi-tray vessel with the blocking mechanism in the manifold as described above enables to perform static culture by attaching the cells on the bottom inner surface of each compartment and rotating the vessel about only a longitudinal axis between 0-90 degrees to perform filling, culturing, infection, transfection, culturing, emptying, sampling, cell detachment and harvesting. It also enables using the same blocking mechanism to perform dynamic culture by attaching the cells to both the top and bottom internal surface of each compartment and rotating the vessel constantly or intermittently about a longitudinal axis between 0-180 degrees to alternately expose the cells directly to gas and submerge the cells in the medium like a roller bottle culture for best oxygenation efficiency. Likewise it can perform the entire culturing processes as described above. When the dynamic culture is applied to the vessel, the upper inner surface of the culture vessel is also fully utilized for culturing cells and thus the productivity is increased further by 2 folds. In other words, the volume of the modified vessel can be reduced by up to 6 folds in total over the current commercial vessels using the static culture method. However, the static culture may be preferable in some cases because of regulatory or some specific culturing requirements.

This disclosure shows that the bioreactor system with moving platform (AMBR1) and fixed platform (AMBR2) using modified multi-tray culture vessels can significantly improve over the manual operation of conventional multi-tray vessel or its commercial automatic cell factory system (AMCF). In the following table is summarized the comparison.

| | | System Features | | | |
|---|---|---|---|---|---|
| | Conventional multi-layer 40 tray vessel Cell Factory or Cellstack | Conventional multi-layer 40 tray vessel Cell Factory, with AMCF system (auto-manipulator) | Conventional multi-layer 40 tray vessel Cell Factory, with AMBR1 | Modified multi-tray vessel I with AMBR1 | Modified multi-tray vessel II (w/o turncock) with AMBR2 |
| Operation | All manual | Semi-automated | Total automation | Total automation | Total automation |
| Controllability | Minimal | Minimal | Maximum | Maximum | Maximum |
| Vessel Size for Equiv. Surface Area (25,280 cm³/vessel) | 47.5 | 47.5 | 47.5 | 15.84 | 15.84 |
| Capital Cost | $100k | $700k+ | Less than $100k | Less than $90k | Less than $80k |
| Labor Intensive? | Yes | Yes | No | No | No |
| Closed System? | No | No | Yes | Yes | Yes |
| Gassing | Passive | Passive | Active | Active | Active |
| platform | NA | NA | See-saw | See-saw | fixed |
| Rotating Action | 3D | 3D | 3D | 3D | 2D |
| Culture Method | Static | Static | Static | Static | Static |
| Function | Limited static culture only | Limited static culture only | Unlimited bioreactor | Unlimited bioreactor | Unlimited bioreactor |
| Separate CO2 Incubator? | Yes | Yes | No | No | No |
| Seeding | Manual | Manual | Auto | Auto | Auto |
| Medium Exchange (Filling/Emptying) | Manual | Auto | Auto | Auto | Auto |
| Infection/Transfection | Manual | Manual | Auto | Auto | Auto |
| Cell Detachment | Manual | Manual | Auto | Auto | Auto |
| Sampling | Manual | Manual | Auto | Auto | Auto |

As disclosed herein the culture vessel is a multi-plate culture vessel comprising a lid, a bottom, at least two sides and two ends each, wherein the culture vessel has only a compartment and at least a flat surface plate, wherein the plate is parallel to the lid and bottom of the culture vessel and configured to secure individually or modularly to the vessel but not sealed and the each plate are freely communicated with other plates; wherein the vessel comprises at least a port configured to allow the active gas and culture fluid to enter and exit the culture vessel, wherein the shape of the vessel is most commonly in circular, oval and rectangular shapes but also in any other polygonal shapes. The each surface plate is individually attached to the vessel or bound together as a module with spacing between the plates by adhesive or thermal press or the likes. The gap between two parallel flat plates can be as narrow as possible but permitting the liquid freely to flow through, preferably, in 1.5 mm to 2.5 mm.

As disclosed herein the each multi-plate culture vessel requires no rotation of the platform in the second axis because there is only one compartment. The rotation in one axis is primary to perform the dynamic culture and oxygenation like roller bottle.

As disclosed herein the each multi-plate culture vessel comprises at least a gas/fluid inlet port configured to allow the respiratory gas and culture fluid to enter the culture vessel, at least a gas/fluid outlet port configured to allow respiratory gas and culture fluid to exit the culture vessel; wherein the outlet port is configured to maintain the volume of culture fluid a half of the vessel during the culturing process. Preferably as shown in FIG. 8A the inlet port 2 is located at a corner of the lid 1a with a perforated tube 2p extended to a half height of the vessel perpendicular to all culture plates 1b and the outlet port 3 is located in the opposite diagonal corner of the lid 1a with a solid open pipe 3p extended to half height of the culture vessel 1. Alternately the outlet port 3 is relocated to the center of one side of the culture vessel 1 with a perforated pipe extended all the way to the opposite side of the vessel parallel to the plate 1 b. In both arrangements the gas and fluid will exit through the tube and the fluid is maintained at constant volume or a half of the height of the vessel or the liquid level 19 when the vessel is in position of RA=0, where the plates are parallel to the ground if there is any addition of fluid during the culturing process. The positive gas enters the gas space of culture vessel through the perforated tube 2p and exit through 3p either at RA=0 or RA=180 as shown in FIG. 8A and FIG. 8B.

As disclosed herein the gap between two parallel flat surface plates of the culture vessel is substantially reduced because there is no gas space required in this disclosed system. The oxygenation is based on the same principle of roller bottle where the cells attached on the plates are directly exposed to air intermittently. A recent new multi-plate bioreactor, Xpansion® manufactured by Pall, uses the similar vessel and utilizes the liquid circulation by pump around the vessel and oxygen transfer by tubing diffusion. The gap between two surface plates is 1.6 mm. However the plates are stationary and only the top surface can be used for cells to attach. Also the oxygen transfer by diffusion through the bulk liquid phase to cells is limited and less efficient as that of this disclosure wherein the cells directly expose to the air for oxygenation rather to the dissolved oxygen in the bulk liquid phase. The culture vessel of this disclosure utilizing both surfaces of a surface plate would create the surface area 2 folds greater than Xpansion®. Furthermore Xpansion® requires a separate incubator for culturing, a harvest station for cell detachment and a lifter and cart for transportation. Like Thermo's automation AMCF system it is not a totally integrated system, it is still risky, labor intensive and extremely expensive. In continuation of the previous disclosure the multi-plate vessel is integrated with a supporting vessel to use it as an incubator and requires no separate temperature control device such as incubator or the likes to perform the unique oxygenation, dynamic culture and all other culture processes in a closed system. This new disclosure shows that the vessel is full of the plates (doubles the surface area), uses the supporting vessel as an incubator, and uses only two ports without baffle. It is totally integrated and performs all culture process automatically in a closed system.

As disclosed herein an automatic multi-plate bioreactor comprising at least a multi-plate culture vessel is intended to perform a dynamic culture utilizing the most efficient oxygenation method. Dynamic culture is a culturing method permitting the medium to move around the cells constantly or intermittently rather than static like the static culture. Each the flat culture surface plate comprises at least two culture surfaces in both sides of each plate, wherein the each flat surface plate are freely communicated with other plates, wherein the each flat surface plate configured to allow cells to attach on both sides, to permit both sides to be exposed to gas space and submerged in medium, alternately and intermittently when the culture vessel is half filled with the culture fluid and is turned alternately between 0 to 180 degrees. Because all flat culture plates are not sealed and separated, the culture fluid always stays in the bottom section of the vessel by gravity as the vessel is turned upside down by 180 degrees. In FIGS. 8A and 8B are shown the sequence of the multi-plate culture vessel to perform the dynamic culture from position RA=0 to RA=180. As the vessel is at RA=0 position, the vessel is filled with culture fluid from a reservoir assembly 33 by a pump apparatus 34 to fill half of the culture vessel 1 at the liquid level 19 and the gas from the gas apparatus 32 enters through port 2$p$ and exits through port 3$p$ in the upper half of the vessel for the cells in this upper section of vessel to perform gas exchange. After a short holding time both inlet and outlet ports 2 and 3 are closed and the culture vessel 1 is turned 180 degrees to the position of RA=180, while the lower half of the culture vessel 1 is emerged to the gas space for gas exchange and the upper half of the plates is submerged to the liquid phase for nutrient replenishment. Similarly the vessel is turned to RA=0 position after a short holding time and the gas ports 2 and 3 are reopened for gas to flow through the space. The rocking motion continues alternately and intermittently throughout the entire culturing period like a roller bottle culture. If there is any addition of fresh medium during the culturing, the port 3 will be opened at position of RA=180 to drain the excess fluid and maintain the fluid volume/level 19 constant at half level of the culture vessel 1. If the medium requires to be replaced or the spend medium to be emptied, the vessel is turned to RA=90 position and the ports 2 and 3 are opened to drain. If the fresh medium is to be filled, the vessel is turned back to RA=0 position to refill.

As disclosed herein the automatic multi-plate bioreactor enables to use the multi-plate culture vessel to perform a batch, fed-batch culture, perfusion culture or batch with recirculation of culture material between vessel and reservoir vessel to perform the control of pH, DO or the likes.

In conclusion, this disclosure shows that the automatic multi-plate bioreactor system can significantly improve over the Xpansion® multi-plate bioreactor system and provide an alternative multi-plate bioreactor system.

What is claimed is:

1. A bioreactor system comprising:
a closed culture vessel comprising:
a multi-tray culture vessel comprising at least two rectangular cell culture compartments having a lid, a bottom, two sides and two ends, arranged in a stacked orientation with respect to each other; and configured to allow cells to attach and grow as a monolayer on the bottom surface;
at least one port for medium or gas in and out of the vessel, wherein each port is in gas/fluid communication among all compartments through a gas/fluid flow pathway for allowing gas/fluid to flow through a manifold and into each culture compartment;
a longitudinal supporting vessel comprising:
a tube positioned to lie along a longitudinal axis of the tube, the tube having ends;
at least one end opening to allow culture material or gas to flow into or out of the tube and the ends;
a platform is configured to hold, secure and manipulate the at least one closed culture vessel;
wherein the platform is a seesaw platform swung along the axis perpendicular to the pivot with the tilting angle of less than 90 degrees in each side of the pivot, wherein the pivot is secured on the tube;
and a driving and rotating assembly configured to rotate and change the position of the supporting vessel and the culture vessel about the longitudinal axis of the tube at an angle position of less than 360 degrees and a holding time, wherein the axis is perpendicular to the first axis swung by the seesaw platform.

2. The bioreactor system of claim 1, wherein the longitudinal supporting vessel shape is selected from the group consisting of circular, oval or rectangular shapes and polygonal shapes.

3. The bioreactor system of claim 1, further comprising:
a reservoir assembly configured to store the supply of gas, culture material, fresh medium, and reagents;
a pumping apparatus configured to pump culture material or gas into and out of the culture vessel through at least one opening of the supporting vessel;
a monitoring apparatus configured to monitor one or more parameters of at least one of the vessel assembly, the driving and rotating assembly, the pumping apparatus, and the gassing apparatus; and
a control apparatus connected wired or wirelessly to the vessel assembly, the reservoir assembly, the pumping apparatus, the gassing apparatus, the gas blending apparatus, the driving and rotating assembly, and the monitoring apparatus, and the control apparatus is further configured to coordinate positioning of the culture and supporting vessels using the driving and rotating assembly with culture material pumping in and out of the culture vessel using the pumping apparatus, pass respiratory gases to enter and exit the culture vessel through the gas port using the gassing apparatus, and to control operating parameters of the supporting vessel monitored by the monitoring apparatus.

4. A bioreactor system comprising:
a closed culture vessel comprising:
a closed culture vessel comprising a lid, a bottom, at least two sides and two ends each and have at least one flat surface for cells to attach and grow as a monolayer at least one port configured to allow the active gas and culture fluid to enter and exit the culture vessel;
a supporting vessel comprising:
a tube positioned to lie along a longitudinal axis of the tube, the tube having ends;
at least one opening to allow culture material or gas to flow into or out of the tube and the ends;

a platform is secured, fixed in stationary position inside of the tube and the ends, wherein the platform is configured to hold, and secure the at least one closed culture vessel;

and a driving and rotating assembly configured to rotate and change the position of the supporting vessel and the culture vessel about the longitudinal axis of the tube at an angle position of less than 360 degrees and holding time.

5. The bioreactor system of claim 4, wherein
the closed culture vessel is a multi-tray culture vessel comprising at least two rectangular cell culture compartments having a lid, a bottom, two sides and two ends, wherein the sides are longer than the ends, arranged in a stacked orientation with respect to each other; and
configured to allow cells to attach and grow as a monolayer on the bottom surface and hold equal amount of medium and gas space above the cells in each compartment; at least one port for medium or gas in and out of the culture vessel, wherein each port is in gas/fluid communication among the compartments through a gas/fluid flow pathway which allows gas/fluid to flow through a manifold and into each culture compartment, and means for opening and blocking at least one gas/fluid communication among the compartments and the flow pathway thereby permitting fluid to flow through a manifold and into each compartment.

6. The bioreactor system of claim 5, wherein said
means for opening or blocking the gas/fluid communication among the culture compartments and the flow pathway allow fluid to flow through a manifold and into each tray by a motorized turncock configured to fit into at least one manifold and to turn on and off the flow of culture fluid.

7. The bioreactor system of claim 4, wherein
the longitudinal supporting vessel shape is selected from the group consisting of circular, oval or rectangular shapes and polygonal shapes.

8. The bioreactor system of claim 4, further comprising:
a reservoir assembly configured to store the supply of gas, culture material, fresh medium, and reagents;
a pumping apparatus configured to pump culture material or gas into and out of the culture vessel through at least one opening of the supporting vessel;
a monitoring/control apparatus configured to control and monitor at least one of the vessel assembly, the driving and rotating assembly, the pumping apparatus, and the gassing apparatus; wherein said control apparatus is connected wirelessly or wired to the vessel assembly, the reservoir assembly, the pumping apparatus, the gassing apparatus, the gas blending apparatus, the driving and rotating assembly, and the monitoring apparatus, and wherein the control apparatus is further configured to coordinate positioning of the culture and supporting vessels using the driving and rotating assembly with control of culture material being pumped into and out of the culture vessel using the pumping apparatus and further permitting gases to enter and exit the culture vessel through the gas port using the gassing apparatus to control operating parameters of the supporting vessel monitored by the monitoring apparatus.

9. The bioreactor system of claim 4, wherein
the closed culture vessel is a multi-plate culture vessel comprising a lid, a bottom, at least two sides and two ends each, wherein the culture vessel includes one compartment and at least one flat surface plate, wherein the plate is parallel to the lid and bottom of the culture vessel and configured to secure but not sealed individually or modularly to the vessel and the each plate are freely communicated with other plates; wherein the vessel comprises at least one port configured to allow the active gas and culture fluid to enter and exit the culture vessel.

* * * * *